(12) United States Patent
Laub et al.

(10) Patent No.: US 11,662,299 B2
(45) Date of Patent: May 30, 2023

(54) METHOD FOR DETERMINING THE ADHESIVE FORCE OF A HEMOSTATIC TISSUE SEALANT PATCH

(71) Applicant: SEALANTIUM MEDICAL LTD, Rosh HaAyin (IL)

(72) Inventors: Orgad Laub, Tel Aviv (IL); Eran Cohen, Hod Hasharon (IL); Yotam Schwartz, Petah Tiqwa (IL)

(73) Assignee: SEALANTIUM MEDICAL LTD, Rosh HaAyin (IL)

( * ) Notice: Subject to any disclaimer, the term of this patent is extended or adjusted under 35 U.S.C. 154(b) by 431 days.

(21) Appl. No.: 17/040,218

(22) PCT Filed: Mar. 19, 2019

(86) PCT No.: PCT/IL2019/050308
§ 371 (c)(1),
(2) Date: Sep. 22, 2020

(87) PCT Pub. No.: WO2019/180713
PCT Pub. Date: Sep. 26, 2019

(65) Prior Publication Data
US 2021/0364415 A1  Nov. 25, 2021

Related U.S. Application Data

(60) Provisional application No. 62/646,409, filed on Mar. 22, 2018.

(51) Int. Cl.
G01N 19/04 (2006.01)
A61F 13/02 (2006.01)
A61F 13/84 (2006.01)

(52) U.S. Cl.
CPC ......... G01N 19/04 (2013.01); A61F 13/0256 (2013.01); *A61F 2013/8491* (2013.01)

(58) Field of Classification Search
CPC ................ G01N 19/04; A61F 13/0256; A61F 2013/8491; A61L 26/00
(Continued)

(56) References Cited

U.S. PATENT DOCUMENTS 5,631,011 A 5/1997 Wadstrom
6,054,122 A 4/2000 MacPhee et al.
(Continued)

FOREIGN PATENT DOCUMENTS

EP 2556842 A1 2/2013
WO 199640174 A1 12/1996
(Continued)

OTHER PUBLICATIONS

International Search Report and Written Opinion PCT/IL2019/050308, dated Jun. 27, 2019.

*Primary Examiner* — Robert R Raevis
(74) *Attorney, Agent, or Firm* — Maschoff Brennan

(57) ABSTRACT

A method for measuring the adhesive strength of a hemostatic tissue patch. Two patches are attached to facing surfaces with a side that would normally seal tissue exposed. Liquid is placed on one of the patches to activate the hemostatic agent, the patches held together long enough to adhere to one another, and then pulled apart. The force necessary to detach them is measured, thereby providing a determination of the adhesive strength of the patch. In contrast to literature methods, the inventive method provides excellent reproducibility.

12 Claims, 2 Drawing Sheets

(58) Field of Classification Search
USPC .............................................. 73/150 A, 827
See application file for complete search history.

(56) References Cited

U.S. PATENT DOCUMENTS

| | | |
|---|---|---|
| 6,056,970 A | 5/2000 | Greenawalt et al. |
| 6,162,241 A | 12/2000 | Coury et al. |
| 6,699,844 B2 | 3/2004 | Jones et al. |
| 7,189,410 B1 | 3/2007 | Drohan et al. |
| 2006/0155235 A1 | 7/2006 | Sawyer |
| 2007/0162121 A1 | 7/2007 | Tarrant et al. |
| 2011/0071498 A1 | 3/2011 | Hakimimehr et al. |
| 2011/0288462 A1 | 11/2011 | Riesinger |
| 2012/0070485 A1 | 3/2012 | Soldani et al. |
| 2017/0157222 A1 | 6/2017 | Ilan et al. |

FOREIGN PATENT DOCUMENTS

| | | |
|---|---|---|
| WO | 199921908 A1 | 5/1999 |
| WO | 2006044882 A2 | 4/2006 |
| WO | 2008019128 A2 | 2/2008 |
| WO | 2014174509 A1 | 10/2014 |

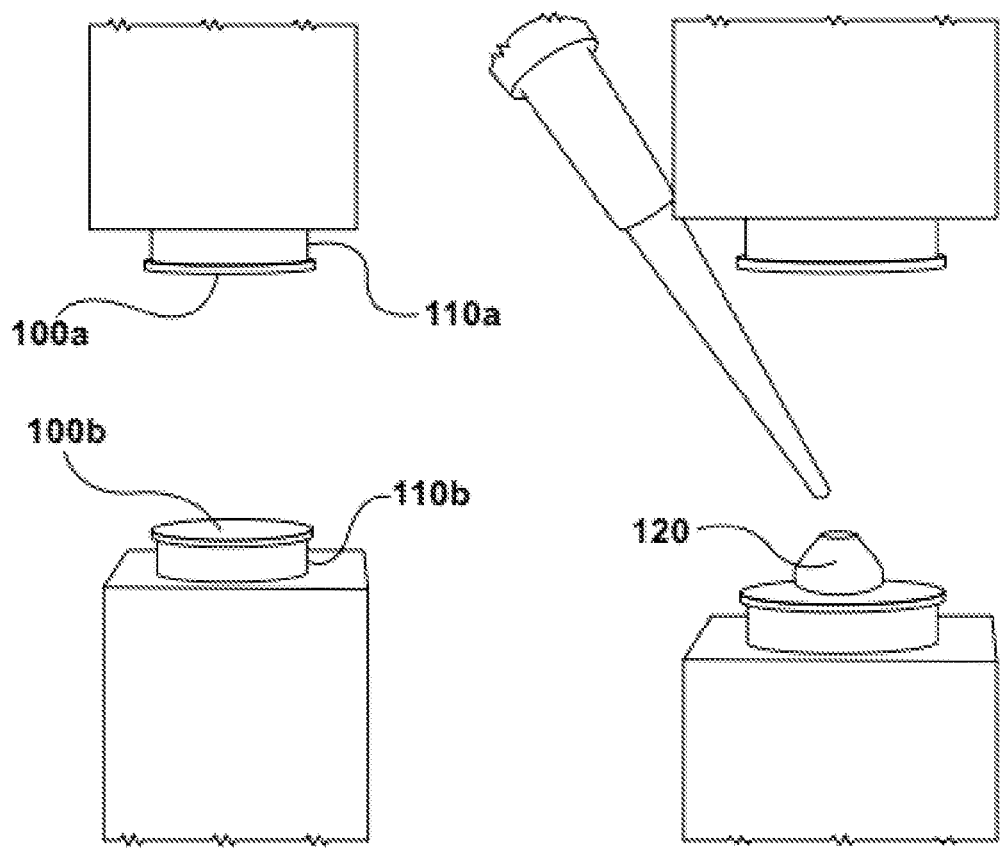
FIG. 1
FIG. 2
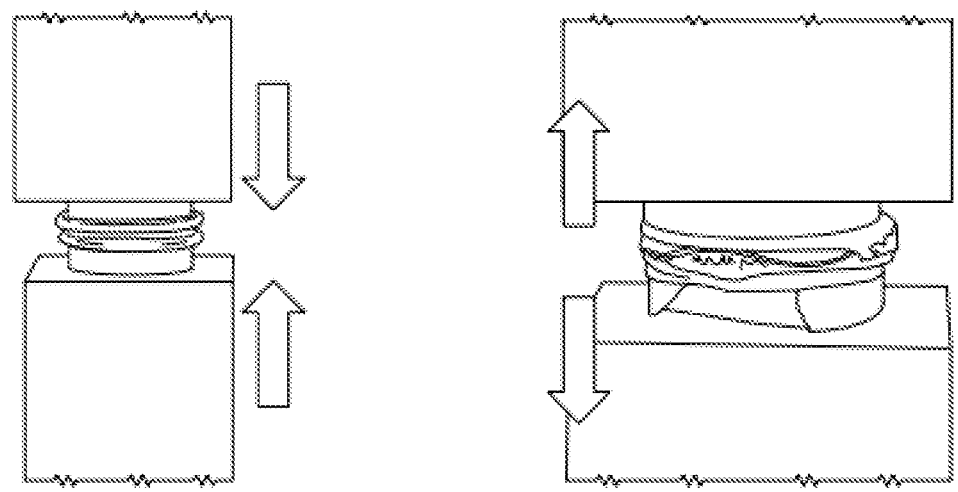
FIG. 3
FIG. 4

METHOD FOR DETERMINING THE ADHESIVE FORCE OF A HEMOSTATIC TISSUE SEALANT PATCH

REFERENCE TO RELATED PUBLICATIONS

This application is a U.S. National Phase entry under 35 U.S.C. § 371 of International (PCT) Appl. No. PCT/IL2019/050308, filed 19 Mar. 2019, and claims priority from U.S. Provisional Pat. Appl. No. 62/646,409, filed 22 Mar. 2018, both of which are incorporated by reference in their entirety.

FIELD OF THE INVENTION

This invention relates in general to measurement of physical properties of tissue sealant patches that incorporate a hemostatic component. It relates in particular to methods for measuring the adhesive strength of such patches.

BACKGROUND OF THE INVENTION

Tissue sealant films and patches that comprise a hemostatic agent such as fibrin or a combination of fibrinogen and thrombin and a backing made of a material such as a biocompatible polymer are well-known in the art. Examples of such films and patches are disclosed, for example, in U.S. Pat. Nos. 5,631,011, 6,054,122, 6,056,970, 6,162,241, 6,699,844, and 7,189,410; PCT (International) Pat. Appl. Pub. Nos. WO96/40174, WO99/21908, WO2006/044882, WO2008/019128, and WO2014/174509; U.S. Pat. Appl. Pub. Nos. 2006/0155235, 2007/0162121, 2011/0071498, 2011/0288462, and 2012/0070485; and European Pat. Appl. Pub. No. 2556842. All of these references are hereby incorporated by reference in their entirety.

It is important, both as a matter of patch design and for quality control, to be able to measure, accurately and reproducibility, the physical characteristics, particularly the adhesive strength, of the tissue sealant patch.

U.S. Pat. No. 6,056,970 discloses a method for measuring the mechanical strength of the patch material, in which a patch is placed in a tensile strength tester and the maximum load at which the material breaks is then determined.

U.S. Pat. Appl. Pub. No. 2007/0162121 discloses that it is possible to determine the adhesive strength of a sealant composition that is used to attach the edges of a protective sleeve to tissue by bonding two plastic tabs with the adhesive formulation and determining the strength of the bonding. No details of the method are provided, and there is no disclosure of a method for measuring the adhesive strength of a patch that comprises a hemostatic material.

U.S. Pat. Appl. Pub. No. 2012/0070485 discloses the use of ASTM method D412-98a for measurement of the tensile strength of the patch material.

European Pat. Appl. Pub. No. 2556842 discloses a qualitative method for determining the adhesion of a tissue sealant compound or a film containing the sealant compound in which the sealant is placed on a glass slide, water is added, a cover slip placed above the sealant, and adhesion verified empirically by observation that the cover slip adhered to the glass slide.

It can thus be seen that a quantitative method that is both accurate and reproducible for determining the adhesive strength of a hemostatic tissue sealant patch remains a long-felt, yet unmet need.

SUMMARY OF THE INVENTION

The invention herein disclosed is designed to meet this long-felt need. The inventors have discovered, surprisingly, that measuring the force required to separate two identical hemostatic tissue sealant patches that are joined by the hemostatic sealant provides a more reliable and reproducible method for measuring the adhesive strength of the patch than methods heretofore known in the art.

It is therefore an object of the present invention to disclose a method for determining the adhesive strength of a hemostatic tissue sealant patch, said hemostatic tissue sealant patch comprising at least one tissue sealing surface and a hemostatic agent, wherein said method comprises:
  attaching a first hemostatic tissue sealant patch to a first surface such that said tissue sealing surface of said first hemostatic tissue sealant patch remains exposed;
  attaching a second hemostatic tissue sealant patch to a second surface such that said tissue sealing surface of said second hemostatic tissue sealant patch remains exposed;
  activating said hemostatic agent on at least one of said hemostatic tissue sealant patches;
  pressing together said tissue sealing surfaces of said hemostatic sealant patches for a first predetermined time, thereby causing said hemostatic sealant patches to adhere one to the other;
  after said first predetermined time, applying a force to said hemostatic patches opposite in direction from that applied in said step of pressing together said tissue sealing surfaces; and,
  measuring the force required to detach fully said hemostatic sealant patches one from the other, thereby determining the adhesive strength of said hemostatic tissue patch.

It is a further object of this invention to disclose such a method, wherein said first and second hemostatic tissue sealant patches are circular and are characterized by an area of 2 cm$^2$.

It is a further object of this invention to disclose the method as defined in any of the above, wherein said steps of attaching said hemostatic tissue sealant patches to said surfaces comprise attaching each of said patches such that a force of at least 50 N is necessary to detach said patch from said surface.

It is a further object of this invention to disclose the method as defined in any of the above, wherein said steps of attaching said hemostatic tissue sealant patches to said surfaces comprise attaching said hemostatic tissue sealant patches by a method selected from gluing and taping with double-sided tape.

It is a further object of this invention to disclose the method as defined in any of the above, wherein said step of activating said hemostatic agent comprises applying a predetermined volume of a fluid to said exposed surface of said first hemostatic tissue sealant patch. In some preferred embodiments of the invention, said step of applying a predetermined volume of a fluid comprises applying a phosphate-buffered saline (PBS) solution to said first hemostatic sealant patch. In some preferred embodiments of the invention, said step of applying a predetermined volume of a fluid comprises applying 125 µl of a 1% PBS solution to said first hemostatic sealant patch.

It is a further object of this invention to disclose the method as defined in any of the above, wherein said step of pressing together said tissue sealing surfaces of said hemostatic sealant patches for a first predetermined time comprises pressing together said tissue sealing surfaces with a force of about 5 N. In some preferred embodiments of the invention, said step of pressing together said tissue sealing surfaces of said hemostatic sealant patches for a first predetermined time comprises pressing together said tissue sealing surfaces with a force of about 5 N for about 3 minutes. In some preferred embodiments of the invention, said step of pressing together said tissue sealing surfaces of said hemostatic sealant patches for a first predetermined time comprises pressing together said tissue sealing surfaces with a force and for a time sufficient to effect adhesion of said patch to tissue.

It is a further object of this invention to disclose the method as defined in any of the above, wherein said step of pressing together said tissue sealing surfaces of said hemostatic sealant patches for a first predetermined time is followed by ceasing to press on said surfaces for a second predetermined time. In some preferred embodiments of the invention, said second predetermined time is about 10 seconds.

BRIEF DESCRIPTION OF THE DRAWINGS

The invention will now be described with reference to the drawings, wherein:

FIG. 1 illustrates the step of attaching patches to opposing surfaces according to one embodiment of the method herein disclosed;

FIG. 2 illustrates the step of adding a fluid to one patch, thereby activating the hemostatic agent according to one embodiment of the method herein disclosed;

FIG. 3 illustrates the method at a point after the step of pressing the two patches together until they adhere one to another, and the direction of motion of the two surfaces as they are pulled apart according to one embodiment of the method herein disclosed;

FIG. 4 illustrates the two patches at the moment that they begin to detach according to one embodiment of the method herein disclosed;

DETAILED DESCRIPTION OF THE PREFERRED EMBODIMENTS

Figure 5:
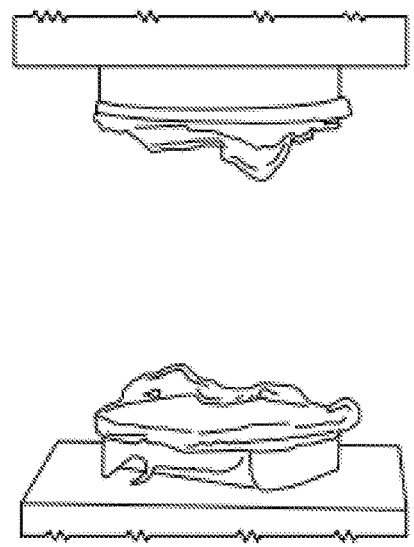
FIG. 5 illustrates the two patches after they have been detached according to one embodiment of the method herein disclosed, demonstrating that the method provides a measurement of the adhesive strength of the side of the patch that would be exposed to tissue; and, FIG. 6 presents a graph showing typical results of measurements of hemostatic tissue patch adhesive strength according to one embodiment of the method herein disclosed.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. All embodiments described herein are therefore to be considered exemplary only and not as restrictive. In addition, in some cases, for clarity or conciseness, different method steps are described separately. All combinations of steps disclosed herein of the inventive method that are not self-contradictory are considered by the inventors to be within the scope of the invention, even if a particular combination is not described explicitly.

As used herein, the term "hemostatic sealant patch" is used to describe a device or composition for stopping, slowing, or preventing leakage of fluid into or out of a body part, that comprises an occlusive material and a hemostatic agent. Non-limiting examples of occlusive materials include biocompatible polymers formed into sheets or films; woven and non-woven materials; etc. Non-limiting examples of hemostatic agent include fibrin and fibrinogen/thrombin mixtures. "Hemostatic sealant patches" as defined herein thus may include devices known alternatively in the literature by such terms as "bandages," "dressings," "films," etc. that comprise the two components listed.

As used herein, the abbreviation "PBS" stands for "phosphate buffered saline."

In the following description, the term "about," when applied to numerical quantities, refers to a range of ±25% of the nominal value.

The inventors have found, surprisingly, that measuring the adhesive force of a hemostatic patch to another similar patch gives more reliable and reproducible results than methods currently known in the art in which the adhesive force of the patch is measured as the force necessary to detach it from a tissue proxy such as meat or from a substance such as glass. Consequently, in the inventive method, two patches are attached one to the other by activation of the hemostatic agent, and the force necessary to separate them is then measured.

Reference is now made to FIGS. 1-5, which are screen captures from a film of one exemplary embodiment of the inventive method, showing the various steps in one preferred embodiment of the method.

Reference is now made to FIG. 1, which illustrates the setup of the measurement. Two hemostatic tissue sealant patches 100a and 100b are attached to two facing surfaces (101a and 101b, respectively) with the side of the patch that in actual use would be in contact with tissue left exposed. The hemostatic tissue sealant patches illustrated in FIG. 1 are of the type disclosed in PCT Pat. Appl. Pub. No. WO2014/174509 (henceforth '509), comprising a thrombin/fibrinogen/$CaCl_2$ hemostatic agent incorporated into one surface of a film made from a polyethylene glycol-polycaprolactone-lactic acid triblock copolymer. For patches in which the hemostatic agent is applied to or incorporated into only one surface, it is this surface that is left exposed for both 100a and 100b. The attachment to the surface may be done by any means that will cause the patch to adhere more strongly to the surface than to the patch itself. In preferred embodiments, the patch is attached to the surface such that the adhesive force is at least 50 N. As one example, the patch can be attached to the surface by using double-sided tape such as cellophane tape or duct tape, or the patch can be glued to the surface. In some embodiments, the two surfaces are the facing surfaces of pistons that are used with, incorporated into, or an integral part of a commercially available material testing machine. Such machines are particularly useful because they provide accurate and reproducible results, and generally can be programmed to perform the method herein disclosed. While the embodiment illustrated in the figure shows the two patches oriented on an axis perpendicular to the table on which the apparatus sits, the method may be used with the patches in any arbitrary absolute orientation as long as the active surfaces are facing one another.

After the two patches have been attached to the facing surfaces, the hemostatic agent is activated. Reference is now made to FIG. 2, which illustrates this step for one embodiment of the method. In this embodiment, an aliquot of liquid 120 is applied to the exposed surface of one of the patches. One non-limiting example of a liquid suitable for use with the inventive method is PBS. Sufficient liquid must be added to activate the hemostatic agent. For example, for the patches illustrated in the figure, which are of the type disclosed in '509 having an area of 2 cm$^2$, a 125 µl aliquot of a 1×PBS solution is sufficient to effect the activation of the hemostatic agent. In the embodiment of the method illustrated in FIG. 2, the liquid is introduced onto the surface of the patch by means of a pipette, but any suitable method for placing the liquid on the patch may be used.

After the hemostatic agent has been activated, the two patches are pressed together. Reference is now made to FIG. 3, which illustrates this step of the method. The two patches are pressed together, i.e. moved toward each other along an axis perpendicular to the facing surfaces until their surfaces touch; the direction of motion is indicated by the arrows in FIG. 3. They are then held together for a time sufficient for the patches to adhere one to the other. In the case of the patches illustrated in the figure, it has been found that pressing the patches together with a force of 5 N for three minutes is sufficient to cause the patches to adhere to one another; these conditions mimic the force and time typically used to attach tissue sealant patches in vivo. In some embodiments of the invention, the force on the patches is relaxed (i.e. no force is applied on the patches in any direction) for a predetermined period of time. This time is generally less than the time during which the patches are pressed together, typically on the order of 10 s.

The two patches are then pulled apart. Reference is now made to FIG. 4, which illustrates this step of the method. Force is applied perpendicular to the facing surfaces in the direction opposite to that used in the previous step, as indicated by the arrows in the figure. In cases in which the measurement is performed on a commercially available materials testing machine, the two pistons are preferably moved apart by setting the machine to move them at a constant speed. The figure illustrates the point at which the two patches just begin to separate. The maximum force measured during the process is recorded as the adhesion force of the patch.

Reference is now made to FIG. 5, which illustrates the system after the measurement is complete. As can be seen in the figure, the two patches remain intact, demonstrating that the measurement is of the adhesive force between the two patches following activation of the hemostatic agent rather than of some other parameter such as the adhesion of the other side of the patch to the piston, the tensile strength of the polymer backing, or the adhesion of the hemostatic material to the polymer backing.

Because the method disclosed herein provides reproducible and accurate measurements of the adhesive strength of hemostatic tissue patches, it can also be used as part of a quality control protocol. Because of the good precision and accuracy of the method, it can be used to determine whether a suspect batch has met a predetermined standard. A standard adhesion is set from measurement of a plurality of patches that are known to have been made according to the proper protocol, and then one or more samples from a suspect batch are tested. If the adhesion of the suspect patches is within the bounds of the standard measurement, then the suspect batch can be assumed to be acceptable to within the standard, whereas if the adhesion of the suspect patches is significantly different from the established standard, then it can be assumed that the suspect patches were not made according to the standard.

EXAMPLES

The following examples are presented to assist a person having ordinary skill in the art to make and use the invention herein disclosed, and are not to be construed as being in any way limiting.

Example 1

A test of the adhesive strength of hemostatic patches of the type disclosed in '509, comprising a hemostatic agent comprising thrombin, fibrinogen, and CaCl$_2$ incorporated into the surface of a polymer backing made from a poly-ethylene-caprolactone-lactic acid triblock copolymer was made. Each of two round patches, each having an area of 2 cm$^2$, was attached by double-sided adhesive tape to the piston of a 10 ml syringe to which a piece of double-sided duct tape had been affixed such that the surface into which the hemostatic agent was incorporated was left exposed. The pistons were affixed to the grips of a Testometric M250 material tester. A 125 µl aliquot of a 1% PBS solution was then placed on the lower patch, followed by pressing together the two patches for 3 minutes with a force of 5 N. The force was then relaxed to 0 N for 10 seconds, following which the grips were moved apart at a constant nominal speed of 50 mm s$^{-1}$. The adhesive strength of the patch was determined as the maximum force necessary for detachment. Results for a series of duplicate runs are given in Table 1. The uncertainty of the average is one standard deviation.

TABLE 1

| Number of Test | Adhesive force, N | Average adhesive force, N |
|---|---|---|
| 1 | 14.664 | 27.625 ± 8.728 |
| 2 | 22.890 | |
| 3 | 30.985 | |
| 4 | 31.407 | |
| 5 | 19.685 | |
| 6 | 34.997 | |
| 7 | 38.745 | |

Example 2

The following example demonstrates both the method disclosed herein and how it can be used for quality control. A batch of patches nominally made in the same manner as those described in the previous example were suspected of having been prepared with an incorrect amount of fibrinogen sealant. As a test, the adhesive strength of several suspect patches was made according to the method disclosed herein and compared with that of patches known to have been made according to the correct protocol and with that of patches into which a 50% excess of fibrinogen sealant was incorporated. The results (adhesive strength in N) are summarized in Table 2.

TABLE 2

| Sample Number | Regular protocol | Extra 50% Sealant | suspect batch |
|---|---|---|---|
| 1 | 24.91 | 17.31 | 20.881 |
| 2 | 35.10 | 14.92 | 17.627 |
| 3 | 29.15 | 14.61 | 18.826 |
| 4 | | | 21.447 |
| Average | 29.72 ± 4.18 | 15.61 ± 1.21 | 19.70 ± 1.54 |

As can be seen from the results summarized in the table, the adhesive strength of the patches in the suspect batch was found to be similar to that of patches into which 50% extra sealant was added, while the adhesive strength of those made according to the regular protocol was to within experimental error identical to that of the patches used in the previous example.

Figure 6:
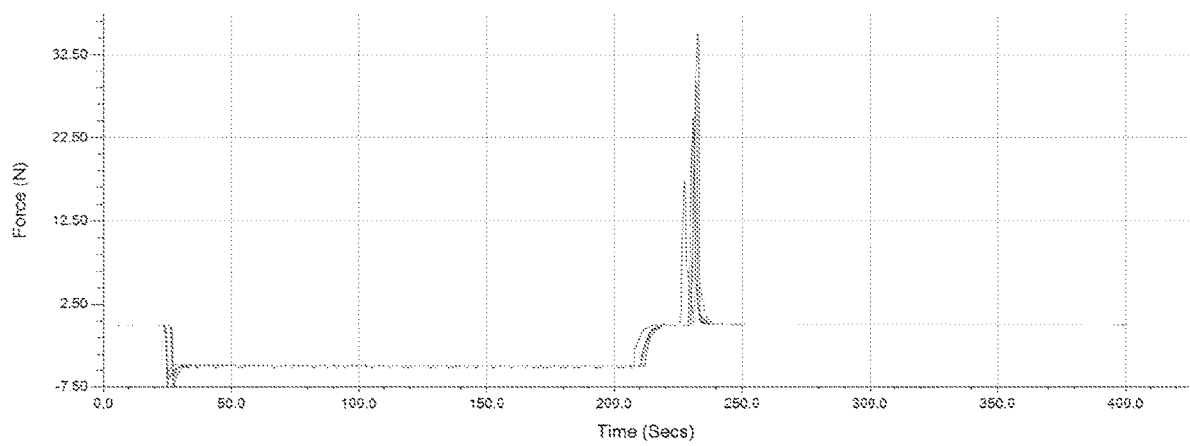

Reference is now made to FIG. 6, which presents a graph showing the results of the measurements reported in Table 2.

We claim:

1. A method for determining the adhesive strength of a hemostatic tissue sealant patch, said hemostatic tissue sealant patch comprising at least one tissue sealing surface and a hemostatic agent, wherein said method comprises:
   attaching a first hemostatic tissue sealant patch to a first surface such that said tissue sealing surface of said first hemostatic tissue sealant patch remains exposed;
   attaching a second hemostatic tissue sealant patch to a second surface such that said tissue sealing surface of said second hemostatic tissue sealant patch remains exposed;
   activating said hemostatic agent on at least one of said hemostatic tissue sealant patches;
   pressing together said tissue sealing surfaces of said hemostatic sealant patches for a first predetermined time, thereby causing said hemostatic sealant patches to adhere one to the other;
   after said first predetermined time, applying a force to said hemostatic patches opposite in direction from that applied in said step of pressing together said tissue sealing surfaces; and,
   measuring the force required to detach fully said hemostatic sealant patches one from the other, thereby determining the adhesive strength of said hemostatic tissue patch.

2. The method according to claim 1, wherein said first and second hemostatic tissue sealant patches are circular and are characterized by an area of 2 cm$^2$.

3. The method according to claim 1, wherein said steps of attaching said hemostatic tissue sealant patches to said surfaces comprise attaching each of said patches such that a force of at least 50 N is necessary to detach said patch from said surface.

4. The method according to claim 1, wherein said steps of attaching said hemostatic tissue sealant patches to said surfaces comprise attaching said hemostatic tissue sealant patches by a method selected from gluing and taping with double-sided tape.

5. The method according to claim 1, wherein said step of activating said hemostatic agent comprises applying a predetermined volume of a fluid to said exposed surface of said first hemostatic tissue sealant patch.

6. The method according to claim 5, wherein said step of applying a predetermined volume of a fluid comprises applying a phosphate-buffered saline (PBS) solution to said exposed surface of said first hemostatic sealant patch.

7. The method according to claim 6, wherein said step of applying a predetermined volume of a fluid comprises applying 125 µl of a 1X PBS solution to said first hemostatic sealant patch.

8. The method according to claim 1, wherein said step of pressing together said tissue sealing surfaces of said hemostatic sealant patches for a first predetermined time comprises pressing together said tissue sealing surfaces with a force of about 5 N.

9. The method according to claim 8, wherein said step of pressing together said tissue sealing surfaces of said hemostatic sealant patches for a first predetermined time comprises pressing together said tissue sealing surfaces with a force of about 5 N for about 3 minutes.

10. The method according to claim 1, wherein said step of pressing together said tissue sealing surfaces of said hemostatic sealant patches for a first predetermined time comprises pressing together said tissue sealing surfaces with a force and for a time sufficient to effect adhesion of said patch to tissue.

11. The method according to claim 1, wherein said step of pressing together said tissue sealing surfaces of said hemostatic sealant patches for a first predetermined time is followed by ceasing to press on said surfaces for a second predetermined time.

12. The method according to claim 11, wherein said second predetermined time is about 10 seconds.

* * * * *